(12) United States Patent
Prusiner et al.

(10) Patent No.: US 6,620,629 B1
(45) Date of Patent: *Sep. 16, 2003

(54) METHOD FOR DETECTING PRIONS

(75) Inventors: Stanley B. Prusiner, San Francisco, CA (US); Jiri Safar, Concord, CA (US)

(73) Assignee: The Regents of the University of California, Oakland, CA (US)

( * ) Notice: Subject to any disclaimer, the term of this patent is extended or adjusted under 35 U.S.C. 154(b) by 134 days.

This patent is subject to a terminal disclaimer.

(21) Appl. No.: 09/699,033

(22) Filed: Oct. 27, 2000

Related U.S. Application Data

(63) Continuation-in-part of application No. 09/235,372, filed on Jan. 20, 1999, now Pat. No. 6,221,614, which is a continuation-in-part of application No. 09/151,057, filed on Sep. 10, 1998, now abandoned, which is a continuation-in-part of application No. 09/026,957, filed on Feb. 20, 1998, now abandoned, which is a continuation-in-part of application No. 08/804,536, filed on Feb. 21, 1997, now Pat. No. 5,891,641.

(51) Int. Cl.$^7$ ............................................. G01N 33/531
(52) U.S. Cl. ............................ 436/543; 436/536; 435/5; 435/7.1
(58) Field of Search ....................... 435/5, 7.1; 436/536, 436/543

(56) References Cited

U.S. PATENT DOCUMENTS

| | | | |
|---|---|---|---|
| 4,300,905 A | 11/1981 | Bleisteiner et al. | |
| 4,320,086 A | 3/1982 | Reiss | |
| 4,806,627 A | 2/1989 | Wisniewski et al. | |
| 5,462,751 A | 10/1995 | Kossovsky et al. | |
| 5,521,060 A | 5/1996 | Hoenes et al. | |
| 5,565,186 A | 10/1996 | Prusiner et al. | |
| 5,846,533 A | 12/1998 | Prusiner et al. | |
| 5,858,326 A | 1/1999 | Kisilevsky et al. | |
| 5,891,641 A | * 4/1999 | Prusiner et al. | 435/7.1 |
| 5,977,324 A | 11/1999 | Prusiner et al. | |
| 6,214,366 B1 | 4/2001 | Prusiner et al. | |
| 6,214,565 B1 | 4/2001 | Prusiner et al. | |
| 2002/0058031 A1 | 5/2002 | Tung | |

FOREIGN PATENT DOCUMENTS

| | | |
|---|---|---|
| AU | 731048 B2 | 11/1997 |
| EP | 0 861 900 A1 | 9/1998 |
| WO | WO 93/10227 | 5/1993 |
| WO | WO 93/23432 | 11/1993 |
| WO | WO 97/16728 | 5/1997 |
| WO | WO 97/40861 | 11/1997 |
| WO | WO 97/43649 | 11/1997 |
| WO | WO 97/46155 | 12/1997 |
| WO | WO 98/00441 | 1/1998 |
| WO | WO 98/16834 | 4/1998 |
| WO | WO 99/42487 | 8/1999 |
| WO | WO 99/42829 | 8/1999 |
| WO | WO 00/02575 | 1/2000 |

OTHER PUBLICATIONS

Max, E. E., 1999, "Immunoglobulins: Molecular Genetics", in *Fundamental Immunology, Fourth Edition*, Paul, W. F., ed., Lippincott–Raven Publishers, Philadelphia, pp. 142–143.*

Williamson, R.A., et al., 1998, "Mapping the prion protein using recombinant antibodies", J. Virol. 72(11):9413–9418.*

Xu, Y., et al., 1997, "Cryptic and regulatory epitopes in CD13/Aminopeptidase N", Exp. Hematol. 25:521–529.*

Yokoyama, T., et al., 1996, "Immunoreactivity of specific epitopes of $PrP^{Sc}$ is enhanced by pretreatment in a hydrated autoclave", Clin. Diag. Lab. Immunol. 3(4):470–471.*

Alpatova, N.M., et al. (1994) "Comparison of Electrochemical Behavior of Heteropolyacids in Solution and Immobilized in a Conducting Polymer Film" *Chemical Abstracts*, vol. 121(16).

Anderson et al., (1996) A Transmission dynamics and epidemiology of BSE in British cattle *Nature*, vol. 382: 779–88.

Barry, R.A., et al., (1986) "Monoclonal Antibodies to the Cellular and Scrapie Prion Proteins," *Journal of Infectious Diseases*, vol. 154:518–521.

Basler et al., (1986) "Scrapie and Cellular PrP Isoforms Are Encoded by the Same Chromosomal Gene," *Cell*, vol. 46: 417–28.

Bendheim, et al., (1984) "Antibodies to a Scrapie Prion Protein," *Nature* 310:418–421.

Bode et al., (1985) "Characterization of Antisera Against Scrapie–Associated Fibrils (SAF) from Affected Hamster and Cross–Reactivity with SAF from Scrapie–Affected Mice and from Patients with Creutzfeldt–Jacob Disease," *J. Gen. Virol.* 66:2471–2478.

Bolton et al., (1982) "Identification of a Protein That Purifies with the Scrapie Prion," *Science* 218: 1309–11.

Brown et al., (1992) "'Friendly Fire' in Medicine: Hormones, Homografts, and Creutzfeldt–Jakob Disease," *Lancet* 340: 24–27.

Buchanan et al., (1991) "Mortality, Neoplasia, and Creutzfeldt–Jakob Disease in Patients Treated with Human Pituitary Growth Hormone in the United Kingdom", *BMJ* 302:824–828.

(List continued on next page.)

*Primary Examiner*—Laurie Scheiner
*Assistant Examiner*—Jeffrey S. Parkin
(74) *Attorney, Agent, or Firm*—Karl Bozicevic; Bozicevic, Field & Francis LLP

(57) ABSTRACT

The present invention provides assays for identifying the levels of both protease sensitive and protease resistant conformers of $PrP^{Sc}$ in a sample. In a preferred embodiment, the assay comprises determining levels of total $PrP^{Sc}$ in a sample, subjecting the $PrP^{Sc}$ fraction to treatment with a protease that selectively hydrolyzes the protease sensitive $PrP^{Sc}$ ($sPrP^{Sc}$) conformers, and quantifying the levels of $sPrP^{Sc}$ in the sample. The ability to detect $sPrP^{Sc}$ allows early detection of prions, since the $PrP^{Sc}$ in easily accessible biological samples such as blood is predominantly $sPrP^{Sc}$. The ratio of $sPrP^{Sc}$ to $rPrP^{Sc}$ also allows the identification of a particular prion strain in an infected sample.

13 Claims, 4 Drawing Sheets

OTHER PUBLICATIONS

Figure 1:
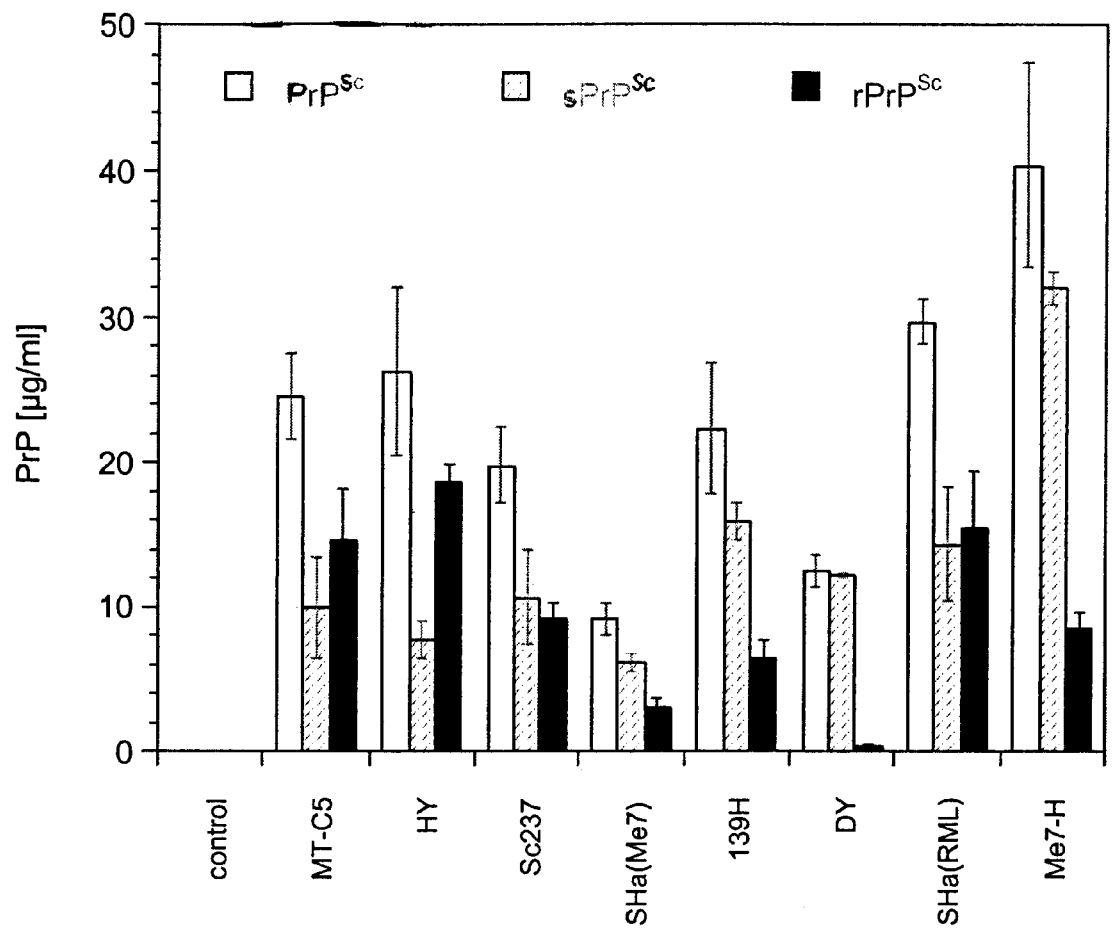

Bueler et al., (1992) "Normal Development and Behavior of Mice Lacking the Neuronal Cell–surface PrP Protein," *Nature* 356:577–582.

Carter et al., (1992) AHigh Level *Escherichia coli* Expression and Production of a Bivalent Humanized Antibody Fragment,@ *Biotechnology* 10:163–7.

Cochius et al., (1992) "Creutzfeldt–Jakob Disease in a Recipient of Human Pituitary–Derived Gonadotrophin: A Second Cage," *J. Neurol. Neurosurg. Psychiatry* 55:1094–1095.

Cochius et al., (1990) "Creutzfeldt–Jakob Disease in a Recipient of Human Pituitary–Derived Gonadotrophin," *Aust. N.Z. J. Med.* 20:592–593.

Collinge, et al., (1996) APrion protein gene analysis in new variant cases of Creutzfeldt–Jakob disease,@ *Lancet* 348: 56.

Gabzion, R., et al. (1988) "Immunoaffinity Purification and Neutralization of Scrapie Prion Infectivity" *Proc. Natl. Acad. Sci. USA*, vol. 85:6617–6621.

Gajdusek, D.C., (1977) "Unconventional Viruses and the Origin and Disappearance of Kuru," *Science* 197:943–960.

Gibbs, Jr. et al., (1993) "Creutzfeldt–Jakob Disease Infectivity of Growth Hormone Derived from Human Pituitary Glands," *N. Engl. J. Med.* 328:358–359.

Goldfarb et al., (1992) "Fatal Familial Insomnia and Familial Creutzfeldt–Jakob Disease: Disease Phenotype Determined by a DNA Polymorphism," *Science* 258:806–808.

Healy et al., "Creutzfeldt–Jakob Disease After Pituitary Gonadotrophins: The Prion is the Problem," *BMJ* (1993) 307:517–518.

Hsiao et al., (1994) ASerial transmission in rodents of neurodegeneration from transgenic mice expressing mutant rion protein, @ *Proc. National Acad. Sci. USA* 91:9126–30.

Kamada, M., et al. (1993) "Dispersion and Fixation of 12–Tungstophosphate Anion on a Silica Surface Modified with Silane Agents Having an Amine Group and Their Catalytic Properties" *Bull. Chem. Soc. JPN.*, vol. 66:3565–3570.

Kascsak, R.J., et al. (1987) "Mouse Polyclonal and Monoclonal Antibody to Scrapie–Associated Fibril Proteins" *Journal of Virology* 61:3688–3693.

Kimberlin, R.H., et al. (1986) "Suppression of Scrapie Infection In Mice by Heteropolyanion 23, Dextran Sulfate, and Some Other Polyanions" *Antimicrobial Agents and Chemotherapy*, vol. 30(3): 409–413.

Lasmezas et al., (1993) "Recombinant Human Growth Hormone and Insulin–Like Growth Factor I Induce PRP Gene Expression in PC12 Cell," *Biochem. Biophys. Res. Commun.* 196:1163–1169.

McKinley et al., (1983) "A Protease–Resistant Protein is a Structural Component of the Scrapie Prion," *Cell* 35:57–62.

Mehlhorn et al., (1996) AHigh–Level Expression and Characterization of a Purified 142–Residue Polypeptide of the Prion Protein,@ *Biochemistry* 35: 5528–37.

Meyer et al., (1986) "Separation and Properties of Cellular and Scrapie Prion Proteins," *Proc. Natl. Acad. Sci. USA* 83: 2310–2314.

Oesch, et al., (1985) "A Cellular Gene Encodes Scrapie PrP 27–30 Protein," *Cell* 40: 735–46.

Pan, et al., (1993) AConversion of α–helices into β–sheets features in the formation of the scrapie prion proteins,@ *Proc. Natl. Acad. Sci. USA* 90:10962–66.

Pan, et al., (1992) "Purification and Properties of the Cellular Prion Protein from Syrian Hamster Brain," *Protein Sci.* 1:1343–1352.

Prusiner, S.B., et al., (1983) "Scrapie prions aggregate to form amyloid–like birefringent rods," *Cell* 35: 349–58.

Prusiner, S.B. et al., ABiology of Prions,@ *The Molecular and Genetic Basis of Neurological Disease*, 2nd Edition, Chap. 7, pp. 103–143.

Rogers et al., (1991) "Epitope Mapping of the Syrian Hamster Prion Protein Utilizing Chimeric and Mutant Genes in a Vaccinia Virus Expression System," *J. Immunol.* 147: 3568–74.

Rogers, et al., (1993) AConversion of truncated and elongated prion proteins into the scrapie isoform in cultured cells,@ *Proc. Natl. Acad. Sci. USA* 90:3182–6.

Safar, J., et al. (1998) "Eight Prion Strains Have PrP$^{Sc}$ Molecules With Different Conformations" *Nature Medicine*, vol. 4(10):1157–1165.

Safar et al. J., (1993) AConformational Transitions, Dissociation, and Unfolding of Scrapie Amyloid (Prion) Protein,@ *J. Biol. Chem.* 268: 20276–84.

Safar, et al., (1990) AScrapie–associated precursor proteins: Antigenic relationship between species and immunocytochemical localization in normal, scrapie, and Creutzfeldt–Jakob disease brains,@ *Neurology* 40:513–7.

Saidkhanov, S.S., et al. (1983) "Changes in Catalytic Properties of 12–Heteropolyacids in Reaction of Dihydrogen Evolution From Water Induced By Their Immobilization on Anion–Exchange Polymers" *Journal of Molecular Catalysis*, vol. 21:365–373.

Schmerr, Mary Jo et al., (1996) "Improvements in a Competition Assay to Detect Scrapie Prion Protein by Capillary Eletrophoresis", *Journal of Chromatography B* 681:29–35.

Serban et al, (1990) "Rapid Detection of Creutzfeldt–Jakob Disease and Scrapie Prion Proteins," *Neurology* 40:110–7.

Stahl et al., (1993) AStructural Studies of the Scrapie Prion Protein Using Mass Spectrometry and Amino Acid Sequencing,@ *Biochemistry* 32: 1991–2002.

Taraboulos et al., (1992) "Regional Mapping of Prion Proteins in Brain," *Proc. Natl. Acad. Sci. USA* 89:7620–7624.

Turk, et al., (1988) "Purification and Properties of the Cellular and Scrapie Hamster Prion Proteins," *Eur. J. Biochem.* 176:21–30.

Wilesmith and Wells, (1991) ABovine Spongiform Encephalopathy,@ *Curr. Topics Microbiol. Immunol.* 172 21–38.

Wilesmith, ABovine Spongiform Encephalopathy,@ *Methods in Molecular Medicines: Prion Diseases*, pp. 155–73.

Williamson, et al., (1996) ACircumventing tolerance to generate autologous monoclonal antibodies to the prion protein,@ *Proc. Natl. Acad. Sci. USA* 93: 7279–82.

Yokoyama, Takashi, et al., (1996) "Immunoreactivity of Specific Epitopes of PrP$^{Sc}$ is Enhanced by Pretreatment in a Hydrated Autoclave", *Clinical and Diagnostic Laboratory Immunology* 3(4):470–471.

Bessen et al. (1992) "Biochemical and Physical Properties of the Prion Protein from Two Strains of the Transmissible Mink Encephalopathy Agent." *J. Virol.* 66(4):2096–2101.

Bessen et al. (1992) "Identification of two biologically distinct strains of transmissible mink encephalopathy in hamsters." *J. Gen. Virol.* 73:329–334.

Collinge et al. (1996) "Molecular analysis of prion strain variation and the aetiology of 'new variant' CJD." *Nature* 383:685–690.

Hill et al. (1997) "Diagnosis of new variant Creutzfeldt–Jakob disease by tonsil biopsy." *The Lancet* 349:99–100.

Karlsson et al. (1991) "Analysis and isolation of human transferrin receptor using the OKT–9 monoclonal antibody covalently crosslinked to magnetic beads" *Anal. Biochem.* 199:219–222.

Kelly (1996) "Alternative conformations of amyloidogenic proteins govern their behavior." *Curr. Op. Struct. Biol.* 6:11–17.

Korth et al. (1997) "Prion ($PrP^{Sc}$)–specific epitope defined by a monoclonal antibody" *Nature* 390:74–77.

Lai et al. (1996) "The Acid–Mediated Denaturation Pathway of Transthyretin Yields a Conformational Intermediate that Can Self–Assemble into Amyloid." *Biochem.* 35:6470–6482.

Marsh et al. (1994) "Physiochemical and biological characterizations of distinct strains of the transmissible mink encephalopathy agent." *Phil. Tran. R. Soc. Lond. B.* 343:413–414.

McCutchen et al. (1993) "Intermolecular Disulfide Linkages are not Required for Transthyretin Amyloid Fibril Formation in vitro." *Biochem. Biophys. Res. Comm.* 197(2):415–421.

McCutchen et al. (1993) "Transthyretin Mutation Leu–55–Pro Significantly Alters Tetramer Stability and Increases Amyloidogenicity." *Biochem.* 32:12119–12127.

Medori et al. (1992) "Fatal Famililal Insomnia, a Prion Disease with a mutation at codon 178 of the prion protein gene." *N. Engl. J. Med.* 326:444–449.

Miroy et al. (1996) "Inhibiting transthyretin amyloid fibril formation via protein stabilization." *Proc. Natl. Acad. Sci. USA* 93:15051–15056.

Prusiner et al. (1997) "The prion diseases of humans and animals" in: *The Molecular and Genetic Basis of Neurological Disease*, $2^{nd}$ ed., Rosenberg et al., eds, Butterworth–Heinemann, Chapter 9.

Prusiner et al. (1982) "Further Purification and Characterization of Scrapie Prions." *Biochem.* 21:6942–6950.

Setchel, C.H. (1985) "Magnetic separations in biotechnology—A review" *J. Chem. Tech. Biotechnol.* 35B:175–182.

Somerville et al. (1997) "Biochemical typing of scrapie strains." *Nature* 386(6625):564.

Telling et al. (1996) "Interactions between wild–type and mutant prion proteins modulate neurodegeneration in transgenic mice." *Genes Devel.* 10:1736–1750.

Telling et al. (1996) "Evidence for the Conformation of the Pathogenic Isoform of the Prion Protein Enciphering and Propagating Prion Diversity." *Science* 274:2079–2082.

* cited by examiner

METHOD FOR DETECTING PRIONS

CROSS-REFERENCE

This application is a continuation-in-part application of Ser. No. 09/235,372, filed on Jan. 20, 1999, now U.S. Pat. No. 6,221,614, which is a continuation-in-part application of Ser. No. 09/151,057, filed Sep. 10, 1998, now abandoned, which is a continuation-in-part of Ser. No. 09/026,957, filed Feb. 20, 1998, now abandoned, which is a continuation-in-part of Ser. No. 08/804,536, filed Feb. 21, 1997, now U.S. Pat. No. 5,891,641, all of which applications are incorporated herein by reference in its entirety and to which applications we claim priority under 35 U.S.C. §120.

GOVERNMENT RIGHTS

The United States Government may have certain rights in this application pursuant to Grant No. AG10770 awarded by the National Institutes of Health.

FIELD OF THE INVENTION

The invention relates generally to methods of detecting prions in samples such as blood or tissue.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects a first species of animal (e.g., a human) will not infect a second species which is genetically diverse form the first species (e.g., a mouse).

A major step in the study of prions and the diseases that they cause was the discovery and purification of a protein designated prion protein ("PrP") (Bolton et al., *Science* 218:1309–11 (1982); Prusiner et al., *Biochemistry* 21:6942–50 (1982); McKinley et al., *Cell* 35:57–62 (1983)). Complete prion protein-encoding genes have since been cloned, sequenced and expressed in transgenic animals. $PrP^C$ is encoded by a single-copy host gene (Basler et al., *Cell* 46:417–28 (1986)) and is normally found at the outer surface of neurons. During a post-translational process, $PrP^{Sc}$ is formed from the normal, cellular PrP isoform ($PrP^C$), and prion diseases result from conversion of $PrP^C$ into a modified isoform called $PrP^{Sc}$. $PrP^{Sc}$ is necessary for both the transmission and pathogenesis of the transmissible neurodegenerative diseases of animals and humans.

See Prusiner, S. B., *Science* 252:1515–1522 (1991). The most common prion diseases of animals are scrapie of sheep and goats, chronic wasting disease of deer and elk, and bovine spongiform encephalopathy (BSE) of cattle (Wilesmith, J. and Wells, *Microbiol. Immunol.* 172:21–38 (1991)). Four prion diseases of humans have been identified: (1) kuru, (2) Creutzfeldt-Jakob Disease (CJD), (3) Gerstmann-Strassler-Scheinker Disease (GSS), and (4) fatal familial insomnia (FFI) (Gajdusek, D. C., *Science* 197:943–960 (1977); Medori et al., *N. Engl. J Med.* 326:444–449 (1992)). The presentation of human prion diseases as sporadic, genetic and infectious illnesses initially posed a conundrum which has been explained by the cellular genetic origin of PrP.

Variations in prions, which cause different disease phenotypes, are often referred to as strains. Each prion strain produces a specific phenotype of prion disease as manifested by the length of the incubation time, the topology of $PrP^{Sc}$ accumulation, and the distribution of pathological lesions (Fraser and Dickinson 1968; Fraser and Dickinson 1973; Bruce, McBride et al. 1989; Taraboulos, Jendroska et al. 1992; DeArmond, Yang et al. 1993; Scott, Groth et al. 1997). Strains replicate with a high degree of fidelity, which demands a mechanism that can account for this phenomenon. That strains could be accounted for because $PrP^{Sc}$ might exist in multiple conformations was postulated, but supporting evidence was initially lacking (Prusiner 1991; Cohen, Pan et al. 1994). Subsequently, different lines of investigation, one on the isolation of prion strains from mink by passage in hamsters (Bessen and Marsh 1994) and the other on the passage of inherited human prion diseases to transgenic (Tg) mice (Telling, Parchi et al. 1996), converged to argue that the properties of prion strains are enciphered in the conformation of $PrP^{Sc}$.

The detection of $PrP^{Sc}$ in biological products is of critical importance, as prion diseases are transmissible. Iatrogenic CJD has been caused by human growth hormone derived from cadaveric pituitaries as well as dura mater grafts (Brown et al., *Lancet* 340:24–27 (1992)). In addition, kuru, which for many decades devastated the Fore and neighboring tribes of the New Guinea highlands, is believed to have been spread by infection during ritualistic cannibalism (Alpers, M. P., *Slow Transmissible Diseases of the Nervous System* Vol. 1, S. B. Prusiner and W. J. Hadlow, eds. (New York: Academic Press), pp. 66–90 (1979)). Numerous young adults treated with HGH derived from human pituitaries have developed CJD (Koch et al., *N. Engl. J Med.* 313:731–733 (1985); Brown et al., *Lancet* 340:24–27 (1992); Fradkin et al., *JAMA* 265:880–884 (1991); Buchanan et al., *Br. Med. J.* 302:824–828 (1991)). In addition, hundreds of children in France have been treated with growth hormone extracted from dead bodies at the risk of developing CJD (see *New Scientist*, Nov. 20, 1993, page 10.) That the HGH prepared from pituitaries was contaminated with prions is supported by the transmission of prion disease to a monkey 66 months after inoculation with a suspect lot of HGH (Gibbs, Jr. et al., *N. Engl. J. Med.* 328:358–359 (1993)).

The long incubation times associated with prion diseases will not reveal the full extent of iatrogenic CJD for decades in thousands of people treated with HGH worldwide. Iatrogenic CJD also appears to have developed in four infertile women treated with contaminated human pituitary-derived gonadotrophin hormone (Healy et al., *Br. J. Med.* 307:517–518 (1993); Cochius et al., *Aust. N. Z. J. Med.* 20:592–593 (1990); Cochius et al., *J. Neurol. Neurosurg. Psychiatry* 55:1094–1095 (1992)) as well as at least 11 patients receiving dura mater grafts (Nisbet et al., *J. Am. Med. Assoc.* 261:1118 (1989); Thadani et al., *J. Neurosurg.* 69:766–769 (1988); Willison et al., *J. Neurosurg. Psychiatric* 54:940 (1991); Brown et al., *Lancet* 340:24–27 (1992)). These cases of iatrogenic CJD underscore the need for screening pharmaceuticals and biological products that might possibly be contaminated with prions.

The importance of detecting prions in biological products has been heightened by the possibility that bovine prions have been transmitted to humans who developed new variant Creutzfeldt-Jakob disease (nvCJD) (G. Chazot et al., *Lancet* 347:1181 (1996); R. G. Will et al. *Lancet* 347:921–925 (1996)). Earlier studies had shown that the N-terminus of $PrP^{Sc}$ could be truncated without loss of Scrapie infectivity (S. B. Prusiner et al., *Biochemistry* 21:6942–6950 (1982); S. B. Prusiner et al., *Cell* 38:127–134 (1984)) and correspondingly, the truncation of the N-terminus of $PrP^{Sc}$ still allowed its conversion into $PrP^{Sc}$ (M. Rogers et al., *Proc. Natl. Acad. Sci. USA* 90:3182–3186 (1993)). The ability of transmission of nvCJD from cattle to humans has been confirmed through in vivo testing, suggesting that the December 20 issue of Proceedings of National Academy of Sciences undermining the comforting presumption that the documented "species barrier" is relevant to this new strain (M. R. Scott et al., *Proc. Natl. Acad. Sci. USA* 96:15137–15142 (1999)).

In view of such, there clearly is a need for a convenient, cost-effective means for identifying prions which cause CJD in biological products, e.g., blood and blood products.

SUMMARY OF THE INVENTION

The present invention provides assays that can identify the levels of both protease sensitive and protease resistant conformers of $PrP^{Sc}$ in a sample. In a preferred embodiment, the assay comprises the steps of 1) determining levels of total $PrP^{Sc}$ in a sample; 2) subjecting the $PrP^{Sc}$ fraction to treatment with a protease that selectively hydrolzes the protease sensitive $PrP^{Sc}$ ($sPrP^{Sc}$) conformers and 3) quantifying the levels of $sPrP^{Sc}$ in the sample. The ability to detect $sPrP^{Sc}$ allows early detection of prions, since the $PrP^{Sc}$ in easily accessible biological samples such as blood is predominantly $sPrP^{Sc}$ and not protease resistant $PrP^{Sc}$, i.e., not $rPrP^{Sc}$. These assay can identify prion infection in a sample prior to the accumulation of the protease resistant $PrP^{Sc}$ ($rPrP^{Sc}$) conformers to a level associated with classic symptoms of prison infection. The present invention thus provides an improved method of early detection of these infectious agents in products such as human biologicals and food.

Methods of the present invention also have the ability to distinguish between different prion isolates ("strains"), and thus can identify a specific prion strain in an infected sample. The ratio of $rPrP^{Sc}$ to $sPrP^{Sc}$ remains relatively constant for each particular strain during prion infection. By determining the levels of $rPrP^{Sc}$ and calculating a ratio $rPrP^{Sc}$ levels to the levels of $sPrP^{Sc}$, a specific prion strain can be identified based on the ratio of in vivo levels of these two $PrP^{Sc}$ conformers.

In one embodiment of the invention, the total $PrP^{Sc}$ fraction is isolated prior to treatment, e.g, by exposing a sample to a complexing agent which selectively binds to $PrP^{Sc}$, e.g., selectively binds to both $rPrP^{Sc}$ and $sPrP^{Sc}$.

In a particular embodiment, the $PrP^{Sc}$ conformers are identified using limited proteinase K digestion followed by indentification by an antibody which recognizes $rPrP^{Sc}$ or $sPrP^{Sc}$, but not both. For example, the concentration of total $PrP^{Sc}$ is measured in a sample by comparing the concentration of $PrP^{Sc}$ to $PrP^{C}$ following limited proteolysis. A second aliquot of a sample is then completely digested (i.e. to remove $PrP^{C}$ and relax the conformation of $sPrP^{Sc}$) and the amount of $rPrP^{Sc}$ measured. The amount of $sPrP^{Sc}$ in a sample can then be determined by substracting the concentration of $rPrP^{Sc}$ from the concentration of total $PrP^{Sc}$.

It is an object of the invention to provide a specific diagnostic assay for prion infection in variable sample material obtained or derived from human, primate, monkey, hamster, mice, pig, bovine, sheep, deer, elk, cat, dog, and chicken tissues.

It is another object of the invention to provide a strain-specific diagnostic and/or prognostic assay for prion infection.

It is yet another object of the invention to identify $PrP^{Sc}$ in the pre-symptomatic stage when proteinase K-resistant forms of $PrP^{Sc}$ are not yet present in phenotypically detectable quantities.

It is yet another object of the invention to provide the disease-specific diagnostic assay for prion infection in the tissues, where the concentration of $rPrP^{Sc}$ is below detectable levels or may not accumulate at all. Examples of such samples are serum and white blood cells (WBC) isolated from prion-infected whole blood.

It is yet another object of the invention to provide a rapid assay to differentiate prion strains in prion-infected animals specifically by determining the ratio of $sPrP^{Sc}$ to $rPrP^{Sc}$ in a sample taken from an infected animal.

One advantage of the present methods is that they are rapid, reliable, and require relatively few reagents or equipment.

An important feature of the assay is the rapid, cost-effective, and high flow-through design with capacity to screen a high volume of samples.

These and other objects, advantages, and features of the invention will become apparent to those persons skilled in the art upon reading the details of the methods as more fully described below.

BRIEF DESCRIPTION OF THE DRAWINGS

FIG. 1 is a graph illustrating prion strain typing by quantification of proteinase K(PK)-sensitive conformer of $PrP^{Sc}$.

FIG. 2 is a graph illustrating detection of $sPrP^{Sc}$ in the brains of Syrian hamsters inoculated interacerebrally with Sc237 prions.

FIG. 3 is a graph illustrating the accumulation of $sPrP^{Sc}$ in the brains of Syrian hamsters inoculated interacerebrally with Sc237 prions precedes the accumulation of $rPrP^{Sc}$.

FIG. 4 is a graph illustrating detection of $sPrP^{Sc}$ in serum and WBC of Syrian hamsters infected with Sc237 prions.

DETAILED DESCRIPTION OF THE PREFERRED EMBODIMENTS

Before the present methods and reagents are described, it is to be understood that this invention is not limited to particular protocols and materials described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sample" includes a plurality of such samples and reference to "the complexing agent" includes reference to one or more complexing agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "complexing agent" is used herein to refer to any material which binds or complexes selectively with either the constrictive conformation of a protein (e.g., with $PrP^{Sc}$) and/or with the relaxed conformation of a protein (e.g., $PrP^c$). This complexing agent may be a biological molecule such as a peptide or antibody, e.g., an antibody selective for $PrP^{Sc}$, or a chemical agent, e.g., phosphotungstic acid (PTA), which may be added in the form of a salt, e.g., sodium phoshotungstate. The complexing agents may be used single or in combination. For example, a biological complexing agent may be used in tandem with a chemical complexing agent, such as the use of a peptide and a chemical agent. In another example, two complexing agents of the same class can be used together, e.g., a mixture of phosphotungstic acid (and salts thereof) and trichloroacetic acid. The complex formed must provide some means for separating the $PrP^{Sc}$ complex from the remainder of the composition, such as immobilization of the complexing agent to a surface. A preferred complexing agent which binds $PrP^{Sc}$ more readily than it binds $PrP^{C}$ and a particularly preferred agent binds $PrP^{Sc}$ with a high degree of affinity and does not bind $PrP^{C}$ at significant levels. Objectively, a preferred binding agent binds $PrP^{Sc}$ with twice or more the binding affinity as it binds $PrP^{C}$ and preferably five times or more the binding affinity as it binds $PrP^{C}$.

The terms "protein" as used herein is intended to encompass any amino acid sequence and include modified sequences such as glycoproteins. The term includes naturally occurring proteins and peptides as well as those which are recombinantly or synthetically synthesized. As used in connection with the present invention the term "protein" is specifically intended to cover naturally occurring proteins which occur in at least two different conformations wherein both conformations have the same or substantially the same amino acid sequence but have three or more different three dimensional structures. The conformations of the protein include at least one conformation which is not related to a disease state and at least two conformations which are related to a disease state, i.e. pathogenic. A specific and preferred example of a protein as used in connection with this disclosure is a PrP protein which includes the non-disease form referred to as the $PrP^{c}$ form and the disease related form referred as the $PrP^{Sc}$, with $PrP^{Sc}$ present in at least one protease-sensitive form ($sPrP^{Sc}$) and one protease resistant conformation ($rPrP^{Sc}$). Although a prion protein or the $PrP^{Sc}$ from of a PrP infectious although it is pathogenic. As used herein, the term pathogenic may mean that the protein actually causes the disease or it may simply mean that the protein is associated with the disease and therefore is present when the disease is present. Thus, a pathogenic protein as used in connection with this disclosure is not necessarily a protein which is the specific causative agent of a disease.

The terms "PrP protein", "PrP" and like are used interchangeably herein and shall mean both the infectious particle form $PrP^{Sc}$ known to cause diseases (spongiform encephalopathies) in humans and animals and the noninfectious form $PrP^{C}$ which, under appropriate conditions is converted to the infectious $PrP^{Sc}$ form.

The terms "prion", "prion protein" and "$PrP^{Sc}$ protein" and the like we used interchangeably herein to refer to the infectious $PrP^{Sc}$ form of PrP, and is a contraction of the words "protein" and "infection." Particles are comprised largely, if not exclusively, of $PrP^{Sc}$ molecules encoded by a PrP gene. Prions are generally $PrP^{Sc}$ dimers. Prions are distinct from bacteria, viruses and viroids. Known prions infect animals to cause Scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-$^{Sc}$heinker Disease (GSS), and (4) fatal familial insomnia (FFI). As used herein "prion" includes all forms of prions causing all or any of these diseases or others in any animals used—and in particular in humans and domesticated farm animals.

The term "PrP gene" is used herein to describe genetic material which expresses proteins including known polymorphisms and pathogenic mutations. The term "PrP gene" refers generally to any gene of any species which encodes any form of a PrP protein. Some commonly known PrP sequences are described in Gabriel et al., *Proc. Natl. Acad. Sci. USA* 89:9097–9101 (1992), and U.S. Pat. Nos. 5,565,186; 5,763,740; 5,792,901; and WO97/04814, incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a $PrP^{C}$ (non-disease) or $PrP^{Sc}$ (disease) form.

The term "antibody" stands for an immunoglobulin protein which is capable of binding an antigen. Antibody as used herein is meant to include the entire antibody as well as any antibody fragments (e.g., F(ab)', Fab, Fv) capable of binding the epitope, antigen or antigenic fragment of interest. Preferred antibodies for assays of the invention are immunoreactive or immunospecific for and therefore specifically and selectively bind to a protein of interest, e.g., a PrP protein and specifically a $PrP^{Sc}$ protein or $PrP^{Sc}$ dimer. Antibodies which are immunoreactive and immunospecific for both the native non-disease form and disease form (e.g., for both native $PrP^{C}$ and native $PrP^{Sc}$) may be used. Antibodies for PrP are preferably immunospecific e.g., not substantially cross-reactive with related materials. Some specific antibodies which can be used in connection with the invention are disclosed in published PCT application WO 97/10505 which is incorporated herein by reference to disclose and describe antibodies. This published PCT application corresponds to U.S. Pat. No. 5,846,533 issued Dec. 8, 1998 also incorporated herein by reference. The term "antibody" encompasses all types of antibodies, e.g., polyclonal, monoclonal, and those produced by the phage display methodology. Particularly preferred antibodies of the invention are antibodies which have a relatively high degree of affinity for both native $PrP^C$ and $PrP^{Sc}$ and those with greater binding affinity for $PrP^{Sc}$ are preferred. An antibody of the invention is a "complexing agent" as defined herein.

An antibody for binding to $PrP^C$ is the monoclonal antibody 263K 3F4 produced by the hybridoma cell line ATCC HB9222 deposited on Oct. 8, 1986 in the American Type Culture Collection, 12301 Parklawn Drive, Rockville, Md. 20852 and disclosed and described in U.S. Pat. No. 4,806,627 issued Feb. 21, 1989—incorporated by reference to disclose antibodies which selectively bind $PrP^c$ but not $PrP^{Sc}$ in its native form (i.e. not protease treated).

"Purified antibody" refers to that which is sufficiently free of other proteins, carbohydrates, and lipids with which it is naturally associated. Such an antibody "preferentially binds" to $PrP^{Sc}$ protein (or an antigenic fragment thereof), and does not substantially recognize or bind to other antigenically unrelated molecules. A purified antibody of the invention is preferably immunoreactive with and immunospecific for a specific species and more preferably immunospecific for native $PrP^{Sc}$.

"Antigenic fragment" of a protein (e.g., a PrP protein) is meant a portion of such a protein which is capable of binding an antibody.

By "binds specifically" is meant high avidity and/or high affinity binding of an antibody to a specific polypeptide, e.g., epitope of a protein, e.g., $PrP^{Sc}$. Antibody binding to its epitope on this specific polypeptide is preferably stronger than binding of the same antibody to any other epitope, particularly those which may be present in molecules in association with, or in the same sample, as the specific polypeptide of interest, e.g., binds more strongly to epitope fragments of a protein such as $PrP^{Sc}$ so that by adjusting binding conditions the antibody binds almost exclusively to an epitope site or fragments of a desired protein such as an epitope fragment of $PrP^{Sc}$.

By "detectably labeled antibody", "detectably labeled anti-PrP" or "detectably labeled anti-PrP fragment" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)). Europium is a particularly preferred label.

Abbreviations used herein include:
CNS for central nervous system;
BSE for bovine spongiform encephalopathy;
CJD for Creutzfeldt-Jacob Disease;
FFI for fatal familial insomnia;
GdnHCl for Guanidine hydrochloride;
GSS for Gerstamnn-Strassler-$^{Sc}$heinker Disease;
Hu for human;
HuPrP for human prion protein;
Mo for mouse;
MoPrP for mouse prion protein;
SHa for a Syrian hamster;
SHaPrP for a Syrian hamster prion protein;
$PrP^{Sc}$ for the Scrapie isoform of the prion protein;
$PrP^C$ for the cellular contained common, normal isoform of the prion protein;
$PrP^{CJD}$ for the CJD isoform of a PrP protein;
FVB for a standard inbred strain of mice often used in the production of transgenic mice since eggs of FVB mice are relatively large and tolerate microinjection of exogenous DNA relatively well;
$sPrP^{Sc}$ for the proteinase K-sensitive fraction of $PrP^{Sc}$;
$tPrP^{Sc}$ for total $PrP^{Sc}$ before proteinase K treatment;
$rPrP^{Sc}$ for the proteinase K-resistant fraction of PrP protein measured after proteinase K treatment and is identical to the originally described PrP 27–30
[DRC]—concentration of a disease related conformation of a protein.
PTA—phosphotungstic acid
NaPTA—sodium phosphotungstate
TCA—trichloroacetic acid
AC—affinity chromatography General Aspects of the Invention The present invention provides a highly sensitive, conformation-dependent immunoassay (CDI) that allows early detection of a particular $PrP^{Sc}$ isoform, $sPrP^{Sc}$ in a sample. This assay can also discriminate between protease-sensitive and protease-resistant conformers of $PrP^{Sc}$ in a sample, and thus quantify the levels of each and thereby the ratio of one form to the other in a particular sample. The methods of the present invention stem from the finding that $PrP^{Sc}$ isoform of PrP exists in at least one conformation that is protease sensitive, designated generally as $sPrP^{Sc}$, and at least one conformation that is protease resistant, designated generally as $rPrP^{Sc}$.

Although the levels of $sPrP^{Sc}$ and $rPrP^{Sc}$ can be determined directly from the sample, in a particular embodiment, an immunoassay of the invention features the steps of 1) isolating total $PrP^{Sc}$ in a sample 2) exposing a portion of this $PrP^{Sc}$ fraction to a protease, e.g., proteinase K; and 3) determining the concentration of the protease resistant and protease sensitive forms of $PrP^{Sc}$ in the sample. The activity of protease is controlled with the $PrP^{Sc}$ fraction for a limited time and under condition such that it is possible to differentiate $sPrP^{Sc}$ from $rPrP^{Sc}$. This conformation-dependent immunoassay provides a rapid tool capable of discriminating the secondary and tertiary structures of a substantial number of $PrP^{Sc}$ molecules. Identification of the protease sensitive form of $PrP^{Sc}$ (i.e., $sPrP^{Sc}$) allows the detection of infectious prions in a sample prior to the accumulation of the protease resistant form in a subject, i.e. while a subject is pre-symptomatic. This will allow the early identification of prions, e.g., in infected animals before they exhibit symptoms, or in a seemingly healthy person.

The methods of the invention can also be used to identify a particular strain of $PrP^{Sc}$, as each strain displays a specific ratio of rPrP$^{Sc}$ to sPrP$^{Sc}$. This assay allows the differentiation of prion strains based on the PrP$^{Sc}$ conformers these strains propagate in vivo. Without being bound to a specific theory, it appears that the protease sensitive conformations of PrP$^{Sc}$ can vary with the particular strain of prion. For example, it has been demonstrated that eight different strains possess at least eight different protease sensitive PrP$^{Sc}$ conformations. In fact, it is believed that each strain is composed of a spectrum of conformations as revealed by limited protease digestion and GdnHCI denaturation studies. These findings contrast with the notion, until recently held, that the primary structure of a protein determines a single tertiary structure (Anfinsen 1973).

The sPrP$^{Sc}$ fraction accumulates together with the rPrP$^{Sc}$ fraction through the pre-symptomatic stage of prion infection, and these two forms are present in a constant ratio in each strain. The ratios are different between strains, however, reflecting the differences in accumulation and clearance of the different conformations of sPrP$^{Sc}$ protein following inoculation. Identification of a particular prion strain in a subject can aid in determining the prognosis of the subject, as each strain is associated with specific disease properties, e.g., an average length of incubation time, the topology of PrP$^{Sc}$ accumulation, and the distribution of lesions produced by that specific prion strain. The presence of a certain strain may also be indicative of the cause of infection, e.g., identifying the strain of prion may help to trace the source of infection of an individual, or to identify the potential source of prions in a contaminated product.

Currently, assays for the detection of prions are in development but not yet commercialized. Further, the cost, convenience or accuracy (on a large scale) of such assays has not yet been determined. Accordingly, when a material such as human plasma is suspected of containing prions it is destroyed—see The Wall Street Journal, Nov. 25, 1998 page 1 article entitled: "'Mad Cow' Fears Leads U.K. to Destroy Parts of all Donated Blood" indicating that England was destroying their supply of human plasma. This dramatic action was taken because (1) prions might be present in their human plasma, (2) prion diseases are fatal and not treatable at present, (3) no commercially available test for prions exists at present, and (4) no commercially available method of removing prions from a sample exists at present. The present invention includes a method of identifying prions in a sample at an early stage of the disease cycle, and a means for establishing the particular strain of prion, which may allow tracing of the product to an infected individual. Moreover, this assay can identify prions in a sample that does not contain rPrP$^{Sc}$ but does have levels of sPrP$^{Sc}$, such as serum and whole blood.

To avoid progression and/or possible transmission of disease, it is important to identify any PrP$^{Sc}$ present in biological fluids, and particularly biological fluids that are to be introduced to a subject (e.g., blood products). The present invention is useful with respect to (1) testing produces such as biologicals and food to ensure that the products do not contain infectious prions, i.e., ensuring that the products are "prion free" and/or (2) identifying a particular strain of prion in a sample to determine the strain of prion responsible for an infection. It is important to know the strain for at least two reasons. First, different strains are treatable via different compounds. Thus, identifying the strain is a first step toward a strain-specific treatment. Second, by knowing the strain it is possible to trace the strain back to its source and thereby determine the source of infection. Knowing the source of an infection is a first step toward developing a plan for stopping the further spread of infection from the identified source.

Procedure in General

Any type of sample can be processed using the present invention in order to identify a pathogenic form of a prion protein and/or to determine the strain of the prion. Although the invention could be applied to the identification of any protein having a constricted and relaxed form, where the constricted form is present in both protease-sensitive conformers (e.g., structural intermediates) and a protease-resistant conformer. The invention is described specifically with respect to identification of the pathogenic form of a PrP protein, and in particular with distinguishing sPrP$^{Sc}$ levels in a sample.

The first step of an assay of the invention is to determine the total amount (or concentration) of disease related protein in a sample unit. For example, this can be done by isolating and physically measuring the tPrP$^{Sc}$ from that unit, or by directly determining the concentration of tPrP$^{Sc}$ in the unit, e.g., by treating the unit with an antibody specific to PrP$^{Sc}$.

A second step of an assay is to treat a unit sample to distinguish the concentration of sPrP$^{Sc}$ and/or rPrP$^{Sc}$ in the sample unit. In one exemplary embodiment, the level of sPrP$^{Sc}$ can be determined by measuring the level of rPrP$^{Sc}$ following treatment of the sample unit and subtracting the level of rPrP$^{Sc}$ from the level of tPrP$^{Sc}$ in that sample unit. For example, a unit of the original sample or the isolated total disease related protein is subjected to a lytic treatment to destroy or hydrolyze all or substantially all protein in the sample except the conformers of the disease related protein resistant to the hydrolytic treatment. In such an example, the sample treatment is carried out in order to (1) hydrolyze all or substantially all non-PrP proteins present in the sample; (2) hydrolyze all or substantially all PrP$^C$ present; (3) hydrolyze protease sensitive PrP$^{Sc}$ present; and (4) hydrolyze the 65 N-terminal amino acids of protease resistant PrP$^{Sc}$ present thereby resistant protein is then determined and subtracted from the total amount of this protease resistant protein is then determined and substracted from the total amount of disease related protein (all PrP$^{Sc}$) to find the concentration of protease sensitive disease related protein (e.g., sPrP$^{Sc}$).

The lytic treatment can include chemical methods such as being exposed to extremes in pH (e.g., 2 or less or 12 or above) strongly reducing or oxidizing compounds. The lytic treatment can also be carried out with temperature. For example, hydrolysis of PrP proteins can be obtained by heating to above 80° C. to 132° C. for 1 to 3 days. The time and temperature can be significantly reduced by raising the-pH to 12 or 13. Combination of time, temperature, pH and chemical compound (e.g., protease) can be adjusted to obtain a desirable result. In various preferred embodiments, the enzyme to protein ratio can vary from 1:5 to 1:500; the pH can vary from 6.5 to 8.5; and the temperature can vary from 22° C. to 37° C.

Alternatively, the sample unit can be treated to unfold the sPrP$^{Sc}$, and levels of sPrP$^{Sc}$ can be determined directly using a binding agent that selectively recognizes the unfolded sPrP$^{Sc}$ and not rPrP$^{Sc}$. For example, chemical methods can unfold the protease sensitive sPrP$^{Sc}$ conformer of PrP$^{Sc}$ and allow antibodies to access an epitope not accessible on treated rPrP$^{Sc}$. The concentration of the treating compounds as well as the time and temperature will vary with the protein being treated and end result to be obtained.

This treatment can be used on the sample directly or on isolated sPrP$^{Sc}$. If the sample unit comprises isolated PrP$^{Sc}$, the levels of sPrP$^{Sc}$ can be measured directly by a binding agent that selectively recognizes the epitope of sPrP$^{Sc}$ that is not accessible on rPrP$^{Sc}$. If the sample unit also contains PrP$^C$ and the binding agent recognizes an epitope available on both PrP$^{Sc}$ and PrP$^C$ (e.g., 3F4), then either the treatment must hydrolyze PrP$^C$ but not sPrP$^{Sc}$ (e.g., limited proteolysis), or levels of PrP$^C$ must be determined prior to treatment. In the latter case the level of binding to the treated sample unit will increase in an amount commensurate with the concentration of sPrP$^{Sc}$.

In addition, physical methods can be used to distinguish between sPrP$^{Sc}$ and rPrP$^{Sc}$. Techniques that are intended to be encompassed in the present methods include, but are not limited to, filtration, ultracentrifugation, chromatography methods based on differences in sedimentation between sPrP$^{Sc}$ and rPrP$^{Sc}$ and methods based on differences in polymerization between sPrP$^{Sc}$ and rPrP$^{Sc}$.

Isolation of tPrP$^{Sc}$ From a Sample Using a Complexing Agent

In a particular embodiment of the invention, prions are isolated from the sample prior to treatment to distinguish rPrP$^{Sc}$ from sPrP$^{Sc}$. For example, prions can be isolated from a biological sample by exposing the sample to a complexing agent, which binds selectively to PrP$^{Sc}$ and allows removal of PrP$^{Sc}$ from that sample. Isolation of PrP$^{Sc}$ may be through complexing with an immobilized complexing agent, i.e. exposure of the sample to an affinity column, membrane, filter, or beads with immobilized complexing agent. The complexing agent will effectively remove the PrP$^{Sc}$ from the sample for further use in the assay.

A biological sample to be treated should be in a liquid flowable form at room temperature (15° C. to 30° C.). The solution should have a pH of about 6.4 to 8.4, preferably 7.4, and should not contain excess magnesium or calcium.

The sample is exposed to a complexing agent which is immobilized on a solid surface or otherwise provided in a manner allowing separation of the prion-bound complexing agent from the sample. The complexing agent forms a complex with or somehow binds preferentially with or exclusively to any constricted (generally a pathogenic form) of the protein present in the sample, thus effectively immobilizing any PrP$^{Sc}$ present in the sample to the solid surface upon exposure of the sample to the immobilized complexing agent.

In one embodiment, a chemical agent such as a heteropoly acid (e.g., PTA), or preferably a metallic salt thereof (NAPTA) is immobilized to a solid surface such as a membrane filter, a magnetic bead, and the like. The sample is subjected to the complexing agent over a period of time sufficient to allow substantially all the PrP$^{Sc}$ in the sample to complex with the PTA. For example, the sample could be incubated at about 30° C. to 45° C. (preferably 37° C.) over a period of from about 1 to 16 hours. The complexing agent forms a complex with the PrP$^{Sc}$. What is important is that complex formed can be separated away from the rest of the sample by some means, e.g. filtration, use of magnetic field, sedimentation and the like.

Complexing Agents

Compounds which are useful as complexing agents in the present invention include antibodies, enzymes, peptides, chemical species, binding molecules, etc. These complexing agents are used in a manner that allows binding and isolation of prions from a biological solutions Such complexing agents may be used in whole blood, in blood components such as plasma and platelets, and in other biological fluids as will be apparent to one skilled in the art.

Chemical Agents

In one embodiment of the invention, the compound for removal of prions from a biological material is a chemical agent that precipitates PrP$^{Sc}$. One preferred class of chemical agents for use as complexing agents in the present invention are heteropoly acids and salts thereof. Heteropoly acids are fully or partially protonated forms of oxyanions having at least one central element and at least one coordinating element. Heteropoly acids may have the Keggin or Dawson structures.

A particular class of heteropoly acids is the protonated form of heteropolymolybdates. These anions contain from 2 to 18 hexavalent molybdenum atoms around one or more central atoms. About 36 different elements have been identified as central atoms of these heteropolymolybdates. These anions are all highly oxygenated. Examples of heteropolymolybdates include $[PMo_{12} O_{40}]^3$, $[As_2Mo_{18} O_{62}]^6$, and $[TeMo_6 O_{24}]^6$, where the central atoms are $P^{5+}$, $As^{5+}$, and $Te^{6+}$, respectively. A more detailed discussion of heteropolymolybdates is provided in the Kirk-Othmer Encyclopedia of Chemical Technology, 3rd ed., 15, 688–689 (1981).

Another class of heteropoly acids, which is analogous to the protonated form of heteropolymolybdates, is the protonated form of heteropolytungstates. In heteropolytungstates, the coordinating element is tungsten instead of molybdenum. U.S. Pat. No. 4,376,219, the entire disclosure of which is expressly incorporated herein by reference, discusses the preparation of various heteropoly acids. The central elements of these heteropoly acids may be selected from the group consisting of P, Si, B, Ge, As, Se, Ti, Zr, Mn, F, V, Ce, and Th. The coordinating elements of these heteropoly acids include Mo and/or W. Optional coordinating elements include V, Mn, Co, Ni, Cu, Zn, and Fe. The ratio of the number of the coordinating elements to the number of central elements may be from 2.5 to 12, preferably from 9 to 12. Particular heteropolyacids, which are exemplified in U.S. Pat. No. 4,376,219, include phosphotungstic acid, silicotungstic acid, 10-tungsto-2-vanadophosphoric acid, 6-tungsto-6-molybdophosphoric acid, phosphomolybdic acid, silicomolybdic acid, germanotungstic acid, tungstofluoric acid, and 18-tungsto-2-phosphoric acid as well as salts of all or any of these acids, e.g., metal salts such as Na, K, Mg, and Ca salts. A particular heteropoly acid for use in the present invention is phosphotungstic acid, i.e., $H_3 PW_{12} O_{40}$ and its metal salts particularly Na salts. Such complexing agents effectively bind to PrP$^{Sc}$.

Such chemical agents may be used alone, in combination, or with other non-bioactive chemicals such as buffers and inert binding chemicals. Heteropoly acids of the invention (e.g., PTA) are preferably, although not exclusively, used in a metallic salt form. The metallic salt includes, but is not limited to, sodium, potassium, calcium and the like.

The amount of heteropoly acid or salt thereof which is combined with the present support material should be present in an amount sufficient to significantly remove PrP$^{Sc}$ from the a biological fluid, and preferably in an amount sufficient to remove PrP$^{Sc}$ to undetectable levels or at least non-infectious levels. The weight ratio of heteropoly acid to support material may be, for example from about 1:20 to about 1:1. The heteropoly acid may be combined with the support material in any manner which provided adequate dispersion of the heteropoly acid, thereby increasing the effective surface area of the heteropoly acid. A preferred technique for combining these components is by impregnation of the support material with the heteropoly acid. The heteropoly acid may also be combined with the support material by an ion exchange technique. The impregnation technique may involve sorbing an aqueous solution of the heteropoly acid into the porous region of the support material followed by drying to remove water and to leave behind supported heteropoly acid. Other methods of immobilizing heteropoly acids or salts thereof may be used to immobilize these complexing agents, as will be apparent to one skilled in the art upon reading this disclosure.

Biological Agents

In another embodiment, the complexing agent is a protein, peptide, or other biological moiety that selectively binds to $PrP^{Sc}$.

In one embodiment, the complexing agents are peptides or other small molecules designed to selectively bind to prions. Preferably, the peptides or small molecules are designed to preferentially bind to $PrP^{Sc}$. By "preferentially bind" is meant that the more preferably 100 times or more, and even more preferably 1000 times or more likely to bind to $PrP^{Sc}$ than to other proteins in the biological solution. Peptides of the invention are preferably designed to bind to the native form of $PrP_{Sc}$, as opposed to the denatured form, since the biological fluids generally contain $PrP^{Sc}$ in native form. Peptides may be designed to maximize binding to $PrP^{Sc}$ by designing the peptides to areas of $PrP^{Sc}$ that are more accessible to binding, as can be predicted by one skilled in the art. Useful antibodies which bind $PrP^{Sc}$ are disclosed and described in U.S. Pat. No. 5,846,533 issued Dec. 8, 1998 incorporated herein to disclose and describe antibodies and methods of making antibodies. Portions of these antibodies which bind to $PrP^{Sc}$ are peptides which can be bound to a support surface and used in the present invention.

The complexing agent of the invention may also be an antibody selective for prions. This antibody may be directly immobilized or may be bound to another component (e.g., a high density metal). That antibody may bind to $PrP^{Sc}$, e.g. the antibody disclosed in U.S. Pat. No. 5,846,533.

In general, scrapie infection fails to produce an immune response, with host organisms being tolerant to $PrP^{Sc}$ from the same species. Antibodies which bind to either $PrP^C$ or $PrP^{Sc}$ are disclosed in U.S. Pat. No. 5,846,533. Any antibody binding to $PrP^C$ and not to $PrP^{Sc}$ can be used to initially isolate the $PrP^{Sc}$ in a sample, and those skilled in the art can generate such using known procedures, e.g., see methods of producing phage display antibody libraries in U.S. Pat. No. 5,223,409. Polyclonal anti-PrP antibodies have though been raised in rabbits following immunization with large amounts of formic acid or SDS-denatured SHaPrP 27–30 (Bendheim, Barry et al., *Nature* 310:418–421 (1984); Bode, Pocchiari et al., *J Gen Virol* 66:2471–2478 (1985); Safar, Ceroni et al., *Neurology* 40:513–517 (1990)). Similarly, a handful of anti-PrP monoclonal antibodies against PrP 27–30 have been produced in mice (Barry and Prusiner, *J Infect Dis* 154:518–521 (1986); Kascsak, Rubenstein et al., *J Virol* 61:3688–3693 (1987)). These antibodies were generated against formic acid- or SDS-denatured PrP 27–30 and are able to recognize native $PrP^C$ and treated or denatured $PrP^{Sc}$ from both SHa and humans equally well, but do not bind to MoPrP. Not surprisingly, the epitopes of these antibodies were mapped to regions of the sequence containing amino acid differences between SHa- and MoPrP (Rogers, Yehiely et al., *Proc Natl Acad Sci USA* 90:3182–3186(1993)).

It is not entirely clear why many antibodies of the type described in the above cited publications will bind to $PrP^C$ and treated or denatured $PrP^{Sc}$ but not to native $PrP^{Sc}$. Without being bound to any particular theory it is believed that such may take place because epitopes which are exposed when the protein is in the $PrP^C$ conformation are unexposed or partially hidden in the $PrP^{Sc}$ configuration— where the protein is relatively insoluble and more compactly folded together.

For purposes of the invention an indication that no binding occurs means that the equilibrium or affinity constant $K_a$ is $10^6$ l/mole or less. Further, binding will be recognized as existing when the $K_a$ is at $10^7$ l/mole or greater, preferably $10^8$ l/mole or greater. The binding affinity of $10^7$ l/mole or more may be due to (1) a single monoclonal antibody (i.e., large numbers of one kind of antibodies) or (2) a plurality of different monoclonal antibodies (e.g., large numbers of each of five different monoclonal antibodies) or (3) large numbers of polyclonal antibodies. It is also possible to use combinations of (1)–(3). Selected preferred antibodies will bind at least 4-fold more avidly to the treated or denatured $PrP^{Sc}$ forms of the protein when compared with their binding to the native conformation of $PrP^{Sc}$. The four fold differential in binding affinity may be accomplished by using several different antibodies as per (1)–(3) above and as such some of the antibodies in a mixture could have less than a four fold difference.

A variety of different methods may be used with one or more different antibodies. Those with skill in the art will recognize that antibodies may be labeled with known labels and used with currently available robotics, sandwich assays, electronic detectors, flow cytometry, and the like. Further, the antibodies may be bound to denser components directly or via other intermediates such as anti-antibodies.

Methods of Purification

The complexing agent of the invention may be used in a variety of purification procedures to effectively isolate prions from a biological material. A number of methods for use in the present invention are summarized as follows.

Affinity Chromatograhy

Affinity chromatography (AC) relies on the interaction of the protein with an immobilized ligand. AC is predicated, in part, on the interaction of ligands attached to chromatographic supports. A hydrophobic ligand coupled to a matrix is variously referred to herein as an AC support, AC gel or AC column. It is further appreciated that the strength of the interaction between the protein and the AC support is not only a function of the proportion of non-polar to polar surfaces on the protein but by the distribution of the non-polar surfaces as well.

A number of matrices may be employed in the preparation of AC columns. Preferably, such matrices are beads, and more preferably spherical beads, which serve as a support surface for the complexing agent of the invention. Suggested materials for the matrices include agarose, cross linked dextran, polyhydroxyl ethyl methacrylate, polyacrylamide, cellulose, and derivatives or combinations thereof, preferably in the form of porous spheres. Cellulose acetate has previously been successfully used in devices for purification of biological fluids, e.g., extracorporeal blood purification devices. Polyurethane is particularly blood compatible. Silica and its derivatives are also especially useful as support material for use with heteropoly acids. See U.S. Pat Nos. 5,475,178 and 5,366,945, which are incorporated herein by reference.

The preferred material for use in the methods of the present invention is agarose, a naturally occurring hydrophilic polymer. A beaded gel with a porosity of from 90–96% is formed by varying the percentage of agarose. The molecular weight of the gel ranges from 0.5 million for 10% agarose to 20 million for 4% agarose. Particle diameters ranging from 20 to 200 microns are commercially available. The mechanical strength of agarose beads can be increased by either increasing the percentage of agarose or crosslinking the beads with epichlorohydrin or 2,3 dibromopropanol, using the method of J. Porath et al. in *J. Chromat* 60, 167 (1971). This allows a corresponding increase in the maximum operating pressure (a fifty percent increase in agarose leads to a two to four fold increase in the maximum operating pressure).

The criteria to determine the appropriate coupling method are: minimization of leakage of the complexing agent from the support, maintenance of the thermal stability of the compound, and retention of the optimum amount of complexing agent. The technique must also not cause a deterioration in the support material or the production of reactive groups on the support which would bind blood components in vivo. The complexing agent must also retain its activity over time.

Further factors which must be considered in optimizing the affinity chromatography coupling method are: the extent of distribution of the coupling agent within the particles and/or columns; pH; temperature; the flow speed of the biological sample through the column; the size of the bound complexing agent; and/or the diameter and pore size of the particular support. Each of these conditions can be optimized for a particular procedure, biological sample, and complexing agent as will be apparent to one skilled in the art.

Filtration Methods

Another method that may be used to remove prions from a biological sample involves filtration through a membrane. The membrane may have the prion complexing agent conjugated directly to the membrane, either on the side facing the biological fluid or more preferably on the side away from the biological fluid. Alternatively, the complexing agent may be compartmentalized in an area behind the membrane which is inaccessible to the larger components of the biological materials, e.g., blood cells. In the latter example, the complexing agent can be bound to an insoluble matrix behind the membrane. The membrane for use in the present invention may be in planar form, in the form of one or more hollow fibers, and/or in the form of flat foils. See U.S. Pat No. 4,361,484, which is incorporated herein by reference.

Suitable materials for the membrane include regenerated cellulose, cellulose acetate, non-woven acrylic copolymer, polysulphone, polyether sulphone, polyacrylonitrile, polyamide and the like. The biologically active material is immobilized in the pores and/or on the surface of the side of the membrane that faces away from the biological fluid. Thereby the components such as blood corpuscles are prevented from contacting the active material. The pores of the membrane are usually of the magnitude of order of 0.01 to 0.8 microns, preferably 0.15 to 0.45 microns. The polymer support must be stable under the conditions of its planned use, i.e., it should not be chemically or enzymatically degraded by blood, the support and immobilized complexing agent must be blood compatible, and the support should have good flow characteristics and low compressibility under clinical flow rates in the range of 150–250 ml/min.

Through the above construction of the microporous membrane, i.e. asymmetric immobilizing of the prion complexing agent, the biological fluid need not be exposed to any following filtering for removing possible remaining harmful residues. As well the separation as the removal of the substances can thereby be performed in one and the same step.

The microporous semipermeable membrane can be in the form of individual fibers which are bundled and encapsulated within one and the same casing, with an inlet and outlet for the biological fluid. The ends of the fibers are glued by means of a suitable binder to retain the individual fibers essentially parallel within the casing. One end of the fibers or bundles of fibers is provided in communication with the inlet, while the opposite end is provided in communication with the outlet.

The biological material is pumped into the casing through the inlet and through the longitudinal void of the fibers and out of the casing through the outlet. During the passage through the casing the fluid is exposed to the pressure variations, such that only a penetrating fraction is caused to flow in an alternating path through the fiber walls in each direction for contacting with the prion complexing material. The means for the realization of the pressure variations may again be made up of an expansion chamber in communication with the space between the individual fibers and bundles of fibers, respectively. Any subsequent filtering of the biological material for the removal of possible harmful residues is not needed, since the filtering is automatically achieved through the passage of the fluid through the fiber walls.

The pressure variations may vary from −200 to +200 mmHg, preferably from −100 to +100 mmHg. The longer the diffusion distance for the blood, for example if the prion complexing agent is bound to an unsoluble matrix behind the membrane, the higher compensating pressure variations are required to achieve the desired separation effect. In a corresponding way the frequency of the pressure variations may vary from about 0.05 up to about 10 Hz, preferably 0.5 to 1 Hz. After the passage through the treating unit the biological material, e.g., whole blood, may reinserted in the patient directly, or may be stored for future use. Treated blood may be stored whole, or may be stored in its various components, e.g., plasma, platelets, erythrocytes, etc. Alternatively, the blood may be separated into its components prior to removal of prions.

When the complexing agent is an antibody, it is often desirable to have a molecular spacer segment forming means for spacing the antibody from the wall of the exterior porous side of the hollow fiber membrane. This general arrangement is preferred when the molecular weight of the antigen is large, e.g., 100,000 Daltons or higher in molecular weight. For example, a six- or eight-carbon methylene group is convenient as a spacer or "handle" between antibody and membrane surface. When an antigen is readily absorbed by albumin or more readily chemically reacted with albumin than with the material of the filter membrane surface, the spacer molecule may be a protein such a albumin. The outer surface of a membrane can be considered a relatively porous material compared to that of the interior surface which is normally the effective filter surface of an ultrafilter membrane of the asymmetric, sometimes called anisotropic, type. Thus, for example, the exterior, porous side of a membrane may be treated with a 17% human albumin solution in saline. The albumin will coat the surfaces within the porous zone of the membrane structure (i.e. the zone that underlies the barrier layer of the membrane) and, thereafter, a solution of protein (e.g., a $PrP^{Sc}$ antibody) can be deposited upon the albumin. Often it is desirable to crosslink the protein somewhat (as with a dilute glutaraldehyde solution or some other such mild crosslink-inducing agent) this aids in anchoring the material in place on the membrane surface.

One approach to preparing a cartridge which is capable of removing pathogenic factors from blood is an extracorporeal circulation system with fiber membranes having sufficient permeability for the pathogenic blood factor to be removed through the membrane and into a soluble, immobilized antibody sequestered in the extrafiber space. This involves the formation of a high molecular weight polymeric conjugate of the PrP$^{Sc}$ antibody and PrP$^{Sc}$ that cannot cross the filtration side of the membrane into the remainder of the biological sample, i.e. where the cells are maintained.

In order to form a soluble, immobilized complexing agent the molecular weight of the immunoreactive complexing agent may be increased to such a size that it will not diffuse, from the exterior, porous, portion of the fiber and into the blood to be purified. This can be done by chemically reacting the complexing agent with a high molecular weight, water-soluble substance such as silica gel or dextran or by polymerizing the immunoreactive complexing agent. The use of such macromolecular-borne antibodies is advantageous for high rate of antigen absorption, due to enhanced rate of polarization effects on mass transfer and binding kinetics.

Alternatively, the membrane may be composed of two membrane halves which are mechanically generally identical to each other but which chemically may be built up of different material. In this case, it is enough if only the membrane half that faces away from the biological material is able to bind to the prion complexing agent. For example, the membrane halves may be provided in an abutting relationship to each other, wherein the PrP$^{Sc}$ complexing agent preferably is bound in the pores and on both surfaces of the membrane half that faces away from the biological material.

The complexing agent (e.g., NaPTA or anti-PrP$^{Sc}$ antibodies) can also be immobilized in the membrane so that the surface that faces towards the biological material is free of the contacting reagent. This is to avoid contact between blood corpuscles and the reagent and thereby pyrogen and/or anaphylactic reactions. Thus it is a form of a symmetric immobilization, where on one surface of the membrane (as well as in the pores) the prion complexing agent is immobilized. The advantage of immobilizing within the pores of the membrane is that the active microscopic surface may be manifolded (>1000) compared to the macroscopic surface. Since the complexing agent is immobilized in the part of membrane that faces away from the biological material the biological material will not come into contact with the material. Consequently, any following separate filtering of the biological material therefore is not necessary.

Alternatively, the prion complexing agent may be bound to an unsoluble matrix behind the membrane. The treating process is yet similar, but since the necessary diffusion distance is about 10 times longer, it may be necessary to arrange a somewhat more real flow through the membrane.

Irrespective of whether the prion complexing agent is immobilized in the pores or immobilized to an insoluble matrix behind the membrane, the immobilizing procedure is preferably performed such that the complex of prions and the complexing agent remains bound and immobilized, i.e. it is not present in the blood following isolation. Generally, covalent coupling is the best immobilization. The nature of covalent coupling used depends on the choice of membrane material and the nature of the complexing agent.

Following immobilization of the prions, the prions may be removed from the complexing agent and/or the binding surface. This is best done by 1) denaturing physical conditions, e.g., pH 2 or pH 12; (2) chaotropic salts such as guanidine hydrochloride (Gdn HCl) or urea; (3) solvents promoting α-helical conformation of the protein such as fluorinated alcohols; or by a combination of such methods. Alternatively, the prions may be left immobilized to the binding surface, and further treated on the matrix itself to differentiate rPrP$^{Sc}$ from PrP$^{Sc}$.

EXAMPLES

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1

Identification of Proteinase K-sensitive PrP$^{Sc}$

Using an assay of the invention proteinase K-sensitive PrP$^{Sc}$ molecules (sPrP$^{Sc}$) with hidden 3F4 epitopes were identified in the brain homogenates of hamsters infected with different prion strains. The sPrP$^{Sc}$ was assessed by subjecting this fraction of PrP$^{Sc}$ that is sensitive to proteolysis to limited digestion with proteinase K, and comparing this and the protease-resistant PrP 27–30 fraction from the total PrP$^{Sc}$ for each of the eight prion strains passaged in Syrian hamsters. The constant proportion of sPrP was a distinct parameter of each individual prion strain in the terminal stage of the disease. When the sPrP$^{Sc}$ fraction was plotted as a function of the incubation time, a linear relationship was found with an excellent correlation coefficient. We hypothetized that sPrP$^{Sc}$ might reflect those PrP$^{Sc}$ molecules that are most readily cleared by cellular proteases. The properties of different conformational isoforms of the PrP protein are summarized in Table 1.

TABLE 1

Conformational isoforms of prion protein

|  | PrP$^C$ | sPrP$^{Sc}$ | rPrP$^{Sc}$ |
| --- | --- | --- | --- |
| Secondary structure | α | unknown | β |
| 3F4 epitope | Exposed | Hidden | Hidden |
| Quaternary structure | Momomer | Unknown | Oligomer |
| Proteinase K | Sensitive | Sensitive | Resistant |
| Relationship of Incubation Time and PrP Concentration | Inverse | Direct | No |
| Infectivity | No | Unknown | Yes |

Example 2

Identification of Prion Stains

The assays of the invention allow prion strain typing by quantification of sPrP$^{Sc}$. First, the size of the protease-resistant PrP$^{Sc}$ fragment (PrP 27–30) was used to distinguish between pairs of prion strains with different biological properties. Since PrP$^C$ and PrP$^{Sc}$ have the same covalent structure, differences in protection against proteolytic degradation of the PrP$^{Sc}$ conformers likely reflects alterations in the tertiary structure of PrP$^{Sc}$. The diminished resistance to proteolysis of PrP$^{Sc}$ from the Dy prion strain, however, did not correlate with prolonged incubation times since several scrapie strains with similar incubation times did not exhibit this decreased protease resistance. Since most prion strains exhibited similar resistance to proteolysis, a more sensitive technique to probe the conformations of PrP$^{Sc}$ from many different strains was developed.

Syrian hamsters were infected by intracerebral injection of the following hamster-adapted Scrapie isolates: Drowsy (Dy), 139H, Hyper (Hy), Me7, MT-C5, and Sc237. The animals were euthanized in terminal stages of disease and their brains immediately frozen and stored at −70° C. Brains were homogenized on ice by 3×30 sec strokes of a Power-Gen homogenizer (Fisher Scientific, Pittsburgh, Pa.) in PBS, pH 7.4. The resulting 10% (w/v) homogenates were spun for 5 min at 500 g in a table-top centrifuge. The supernatant was mixed 1:1 with 4% Sarcosyl in PBS, pH 7.4. Each sample was divided in two aliquots: (a) untreated, and (b) treated with 50 μg/ml of Proteinase K (PK) for 2 h at 37° C.

After blocking the reaction with 0.5 mM PMSF and Aprotinin and Leupeptin (2 μg/ml each), each sample was again divided into two aliquots: (1) untreated, designated native; (2) mixed to a final concentration of 4M GdnHCl and heated for 5 min at 80–100° C., designated denatured. Both samples were diluted 20-fold by H$_2$O and aliquots loaded on a polystyrene plate activated for 1 h with 0.2% glutaraldehyde in PBS. The plates, incubated overnight at 5° C., were blocked with TBS, pH 7.8, containing 0.5% BSA (w/v) and 6% Sorbitol (w/v). In the next step, they were washed three times with TBS, pH 7.8 containing 0.05% (v/v) of Tween 20 and incubated for 2 h with Europium-labeled monoclonal antibody 3F4. The plates were developed after an additional seven washing steps in an enhancement solution provided by the Europium label supplier (Wallac Inc, Turku, Finland) and signal counted on DELFIA 1234 Fluorometer (Wallac Inc, Turku, Finland). The PrP$^{Sc}$ content was calculated as described (Safar, Wille et al. 1998).

As determined by the assays, PrP$^{Sc}$ of each hamster-adapted prion strain displays different proteolytic sensitivity. The data points and bars represent average±SEM obtained from three different brains infected with each prion strain (FIG. 1). This difference in sensitivity also, each strain has different overall PrP$^{Sc}$ levels, as well as different ratios of rPrP$^{Sc}$ to sPrP$^{Sc}$.

Example 3

Early Detection of sPrP$^{Sc}$ in Brain Homogenates

The assays allowing detection of sPrP$^{Sc}$ were also effective in early detection of of sPrP$^{Sc}$ in the brains of Syrian hamsters inoculated interacerebrally with Sc237 prions. The Proteinase K treated or untreated aliquots of brain homogenates were first precipitated with sodium phosphotungstate and the concentration of PrP$^{Sc}$ in the pellet was determined before and after Proteinase K treatment as described in Example 2.

Figure 2:
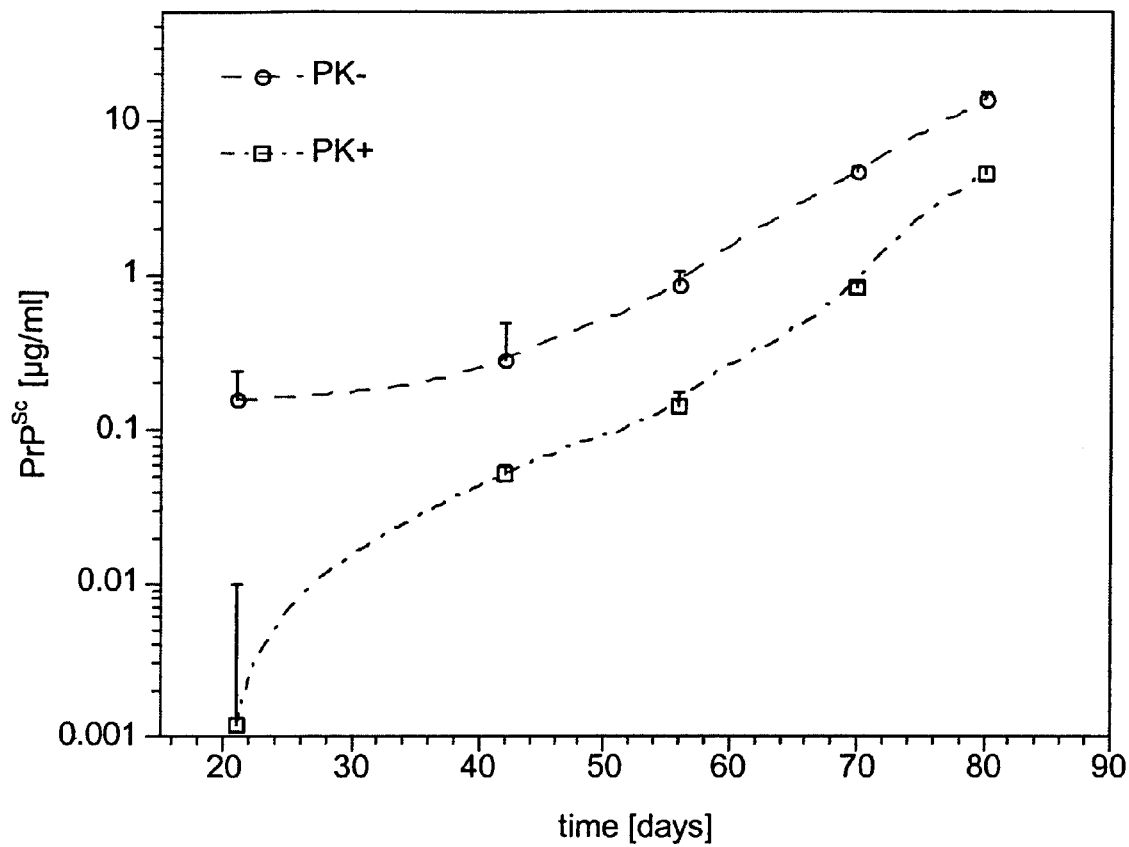

Accumulation of sPrP$^{Sc}$ in the brains of Syrian hamsters inoculated interacerebrally with Sc237 prions precedes the accumulation of rPrP$^{Sc}$. As shown in FIG. 2, sPrP$^{Sc}$ was detectable as early as 20 days post infection, whereas the level of rPrP$^{Sc}$ was very low at that time point. The sPrP$^{Sc}$ fraction apparently accumulates together with rPrP$^{Sc}$ through the pre-symptomatic stage of the Sc237 prion infection, with little variation in the percentage of sPrP$^{Sc}$ of total PrP$^{Sc}$. Moreover, the CDI data on hamsters infected with different prion strains confirms the belief that the proportion of sPrP$^{Sc}$ versus rPrP$^{Sc}$ is a constant and strain-specific quantitative feature of prion replication. The data points and bars represent average±SEM obtained by CDI from three different brains infected with Sc237 prions.

Figure 3:
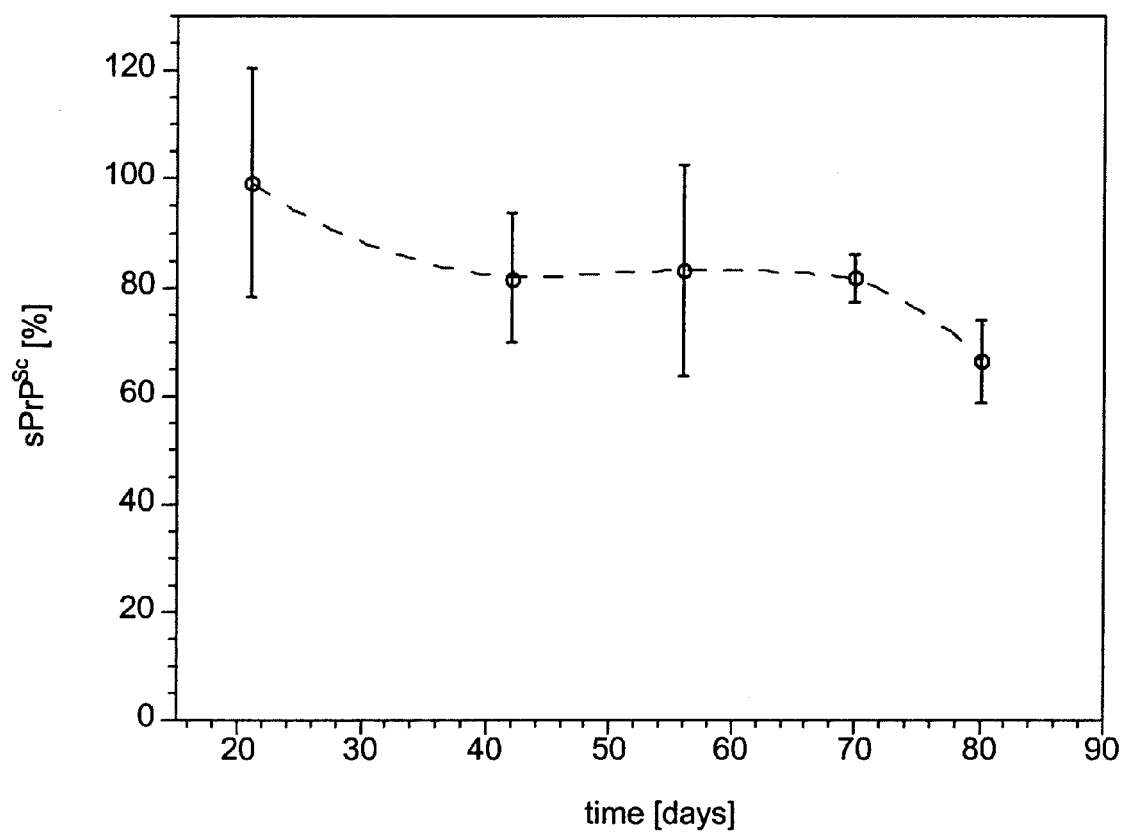

When expressed as a fraction of total PrP$^{Sc}$, sPrP$^{Sc}$ is present as a large fraction of total PrP$^{Sc}$ from the period of 20 days to 80 days post-inoculation (FIG. 3). These results demonstrate that most of the intracerebral inoculum, which is presumably predominantly rPrP$^{Sc}$, is rapidly cleared out within days after inoculation. The data points and bars represent average±SEM obtained from three different brains infected with Sc237 prions.

Example 4

Identification of sPrP$^{Sc}$ in Biological Liquids

Assays of the invention were also used to show that the PrP$^{Sc}$ present in prion infected white blood cells (WBC) and serum is proteinase K-sensitive (sPrP$^{Sc}$). Individual blood fractions from age-matched controls (c) or Sc237 infected animals (Sc) were assayed by CDI before and after Proteinase K (PK) treatment.

The whole blood obtained from normal (c) or Syrian hamsters infected with Sc237 prions (Sc) was mixed (1:9) with 3.8% (w/v) buffered sodium citrate, pH 7.2, and spun at 1100 rpm to obtain plasma. Cellular elements were then separated into different fractions by Percoll gradient (Pharmacia). To obtain serum, the Syrian hamster blood obtained from normal (c) or Scrapie-infected Syrian hamsters (Sc) was clotted in borosilicate glass tubes. Serum was separated from the clot by centrifugation at 500 g. After adding 2% Sarkosyl, each blood fraction was divided into two aliquots: (a) untreated and (b) treated with 25 μg/ml of proteinase K (PK) for 1 h at 37° C. After adding 0.3–1.2% (w/v) sodium phosphotungstate, and 35–50 mM MgCl$_2$, all samples were incubated overnight at 37° C. and spin at 14,000 g. The pellet was resuspended and divided into native and denatured aliquot as described in Example 2. Each aliquot was first incubated on R1 antibody-coated ELISA plates and developed with Europium labeled 3F4 monoclonal antibody. After seven washing steps, the signal was evaluated with Discovery (Packard Inc.) time-resolved fluorescence spectroscopy.

Figure 4:
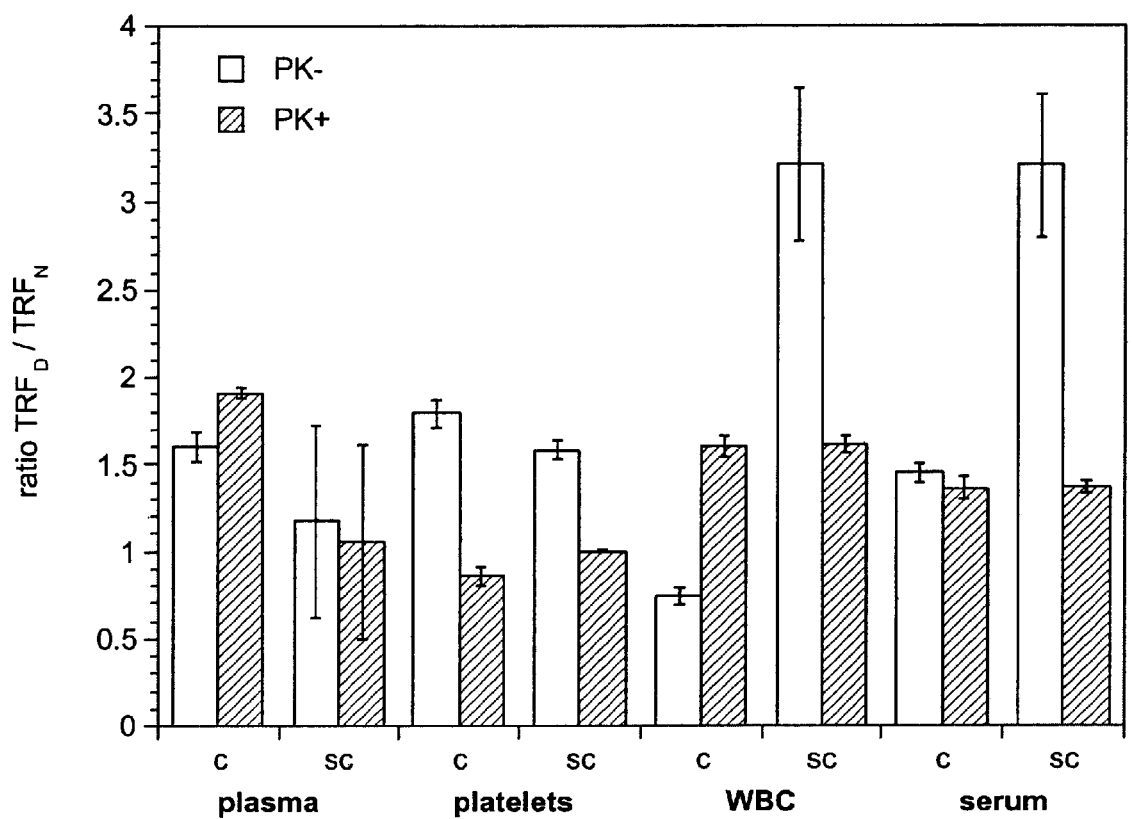

The results were expressed as a ratio of the signals from denatured (TRF$_D$) and native (TRF$_N$) aliquots of each sample (FIG. 4). While sPrP$^{Sc}$ was present in plasma and platelets at nearly the same levels as rPrP$^{Sc}$, sPrP$^{Sc}$ was the predominant fraction of PrP$^{Sc}$ in whole blood cells and serum, and the levels were much higher than those found in plasma or platelets. Values of the CDI ratio exceeding 2 indicate a detectable presence of PrP$^{Sc}$.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of identifying prion infection in a sample, comprising:

determining a total amount of PrP$^{Sc}$ in a unit of sample;

subjecting the sample to a treatment with proteinase K under conditions sufficient to expose an epitope on sensitive PrP$^{Sc}$ (sPrP$^{Sc}$) in the sample, wherein the epitope renders the sPrP$^{Sc}$ detectable by a detectably labeled 3F4 antibody;

contacting the sample with a detectably labeled 3F4 antibody; and determining the binding of the detectably labeled 3F4 antibody to the sPrP$^{Sc}$;

wherein the binding of the binding agent to the treated sPrP$^{Sc}$ is indicative of the presence of infectious prions in a sample.

2. The method of claim 1, wherein the sample is selected from the group consisting of human serum and human whole blood.

3. The method of claim 1, wherein the sPrP$^{Sc}$ is present in the sample in a concentration of $1 \times 10^3$ particles/ml or less.

4. A method of determining the strain of PrP$^{Sc}$ in a sample, comprising:

determining a total amount of PrP$^{Sc}$ in a unit of sample;

subjecting the sample to a treatment with proteinase K under conditions sufficient to expose an epitope on sensitive PrP$^{Sc}$ (sPrP$^{Sc}$) in the sample, wherein the epitope renders the sPrP$^{Sc}$ detectable by a detectably labeled 3F4 antibody;

contacting the sample with detectably labeled 3F4 antibody; and determining the binding of the detectably labeled 3F4 antibody to the sPrP$^{Sc}$;

wherein the binding of the binding agent to the treated sPrP$^{Sc}$ is indicative of the presence of infectious prions in a sample;

determining the ratios of sPrP$^{Sc}$ to total PrP$^{Sc}$; and comparing the determined ratio to a known ratio of a known strain of PrP$^{Sc}$ to thereby determine the strain of PrP$^{Sc}$ in the sample.

5. A method of determining sensitive PrP$^{Sc}$ protein (sPrP$^{Sc}$) in a sample, comprising:

determining an amount of total PrP$^{Sc}$ in a unit amount of the sample;

subjecting an amount of the sample to treatment with proteinase K under condition sufficient to hydrolyze substantially all sPrP$^{Sc}$ and provide a treated amount of sample;

determining an amount of resistant PrP$^{Sc}$ protein (rPrP$^{Sc}$) in a unit amount of the treated sample; and subtracting the amount of rPrP$^{Sc}$ in a unit amount of the sample from the total PrP$^{Sc}$ in a unit amount of the sample to calculate an amount of sPrP$^{Sc}$ in a unit amount of the sample.

6. The method of claim 5, wherein the sample is animal derived.

7. The method of claim 6, wherein the rPrP$^{Sc}$ comprises PrP 27–30.

8. The method of claim 7, wherein the amount of total PrP$^{Sc}$ and amount of rPrP$^{Sc}$ are determined using a methodology capable of detecting a protein concentration over a range of five orders of magnitude or more.

9. The method of claim 5, further comprising:

isolating PrP$^{Sc}$ in the sample prior to subjecting the sample to treatment.

10. The method of claim 9, wherein the isolating comprises contacting the sample with a metal salt of phosphotungstic acid.

11. The method of claim 7, wherein the animal is extracted from a cow.

12. The method of claim 7, wherein the animal is extracted from a human.

13. The method of claim 5, further comprising:

calculating a ratio of sPrP$^{Sc}$ to rPrP$^{Sc}$.

UNITED STATES PATENT AND TRADEMARK OFFICE
CERTIFICATE OF CORRECTION

PATENT NO. : 6,620,629 B1
DATED : September 16, 2003
INVENTOR(S) : Prusiner, Stanley B. et al.

It is certified that error appears in the above-identified patent and that said Letters Patent is hereby corrected as shown below:

<u>Column 22,</u>
Line 32, please change the word "animal" to -- sample --; and
Line 34, please change the word "animal" to -- sample --.

Signed and Sealed this

Third Day of May, 2005

JON W. DUDAS
*Director of the United States Patent and Trademark Office*